(12) United States Patent
Karim et al.

(10) Patent No.: US 9,271,813 B2
(45) Date of Patent: Mar. 1, 2016

(54) DIGITALLY-PAINTED DENTAL ARTICLES

(75) Inventors: Naimul Karim, Maplewood, MN (US); Sumita B. Mitra, West Saint Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 666 days.

(21) Appl. No.: 12/741,631

(22) PCT Filed: Nov. 20, 2008

(86) PCT No.: PCT/US2008/084138
§ 371 (c)(1),
(2), (4) Date: May 6, 2010

(87) PCT Pub. No.: WO2009/070482
PCT Pub. Date: Jun. 4, 2009

(65) Prior Publication Data
US 2010/0260924 A1    Oct. 14, 2010

Related U.S. Application Data

(60) Provisional application No. 60/990,680, filed on Nov. 28, 2007.

(51) Int. Cl.
*A61C 13/00* (2006.01)
*A61C 13/08* (2006.01)

(52) U.S. Cl.
CPC ............ *A61C 13/0019* (2013.01); *A61C 13/082* (2013.01)

(58) Field of Classification Search
CPC .......................... A61C 13/001; A61C 13/0012
USPC ................................................ 427/2.26, 2.29
See application file for complete search history.

(56) References Cited

U.S. PATENT DOCUMENTS

| | | | |
|---|---|---|---|
| 4,585,417 A | 4/1986 | Sozio et al. | |
| 5,944,893 A | 8/1999 | Anderson | |
| 5,972,111 A * | 10/1999 | Anderson | 118/300 |
| 6,190,454 B1 | 2/2001 | Anderson | |
| 6,358,047 B2 * | 3/2002 | Lehmann | 433/26 |
| 7,086,863 B2 * | 8/2006 | Van der Zel | 433/223 |
| 2003/0114553 A1 | 6/2003 | Karim et al. | |
| 2004/0133293 A1 | 7/2004 | Durbin et al. | |
| 2005/0042576 A1 | 2/2005 | Oxman et al. | |
| 2005/0042577 A1 | 2/2005 | Kvitrud et al. | |
| 2005/0070782 A1 | 3/2005 | Brodkin | |
| 2005/0100868 A1 | 5/2005 | Karim et al. | |
| 2005/0147944 A1 | 7/2005 | Karim et al. | |
| 2006/0008777 A1 * | 1/2006 | Peterson et al. | 433/223 |

(Continued)

FOREIGN PATENT DOCUMENTS

| | | |
|---|---|---|
| CN | 1451367 | 10/2003 |
| JP | 2003340813 | 12/2003 |
| WO | WO 2006/036114 | 4/2006 |
| WO | WO 2006036114 A1 * | 4/2006 |
| WO | WO 2007/083372 | 7/2007 |

*Primary Examiner* — Cachet Sellman

(57) ABSTRACT

A digital painting process provides computer-controlled finishing of dental articles. The process can selectively apply different materials over portions of a dental article in one or more layers to achieve a multi-chromatic finish having a variety of colors, finishes, and surface properties that closely match the appearance and function of human dentition.

8 Claims, 2 Drawing Sheets

(56) References Cited

U.S. PATENT DOCUMENTS

| | | |
|---|---|---|
| 2006/0240177 A1 | 10/2006 | Newkirk et al. |
| 2007/0103460 A1 | 5/2007 | Zhang et al. |
| 2007/0172101 A1 | 7/2007 | Kriveshko et al. |
| 2007/0182797 A1 | 8/2007 | Free et al. |
| 2007/0188769 A1 | 8/2007 | Rohaly et al. |
| 2008/0015727 A1 | 1/2008 | Dunne et al. |
| 2008/0153067 A1 | 6/2008 | Berckmans et al. |
| 2008/0318189 A1* | 12/2008 | Brodkin et al. ............... 433/223 |

* cited by examiner

DIGITALLY-PAINTED DENTAL ARTICLES

CROSS REFERENCE TO RELATED APPLICATIONS

This application is a national stage filing under 35 U.S.C. 371 of PCT/US2008/084138, filed Nov. 20, 2008, which claims priority to U.S. application Ser. No. 60/990,680, filed Nov. 28, 2007, the disclosure of which is incorporated by reference in its/their entirety herein.

BACKGROUND

1. Field of the Invention

The invention relates to dentistry, and more particularly to coating dental articles such as restorations using a digitally-controlled painting process.

2. Description of the Related Art

A number of techniques have been devised for automated fabrication of dental articles such as restorations, prostheses, and the like. While these techniques reduce the manual steps involved in creating dental articles and may improve the spatial fidelity to a CAD model or original dentition, they still require significant manual labor when finishing products to match the appearance and function of natural dentition.

There remains a need for automated finishing of dental articles.

SUMMARY

A digital painting process provides computer-controlled finishing of dental articles. The process can selectively apply different materials over portions of a dental article in one or more layers to achieve a multi-chromatic finish having a variety of colors, finishes, and surface properties that closely match the appearance and function of human dentition.

In one aspect, a method disclosed herein includes fabricating an understructure for a dental article using an additive process, the dental article including a volume having a bonding surface shaped to attach to a site in human dentition and a functional surface shaped to replace a dental structure removed from the site; and adding at least one layer to the understructure using a digital painting process.

The understructure may include a majority of the volume of the dental article. The method may include receiving a digital model of the dental article and digitally fabricating the understructure from the digital model. The additive process may include one or more of stereolithography, digital light processing, and three-dimensional printing. The understructure may be uncured, and the method may include curing the understructure after fabricating the understructure and before adding at least one layer. The understructure may be uncured, and the method may include curing the understructure after adding at least one layer. Adding at least one layer may include adding a plurality of layers using the digital painting process. The plurality of layers may include two or more different materials. The two or more different materials may have a color and an opacity selected to provide the dental article with an appearance similar to the dental structure removed from the site. Adding at least one layer may include adding at least one layer to the functional surface that includes two or more different materials in two or more regions of the functional surface. The two or more different materials may each have a different opacity. The two or more different materials may each have a different color. The method may include curing the at least one layer to provide a cured layer. Curing may include exposing the at least one layer to one or more of light, electromagnetic waves, heat, vacuum, and pressure. Curing the at least one layer may include applying numerous cycles of curing conditions. The method may include adding at least one additional layer to the cured layer. The method may include partially curing the at least one layer to provide a partially cured layer before adding at least one additional layer to the partially cured layer using the digital painting process. The dental article may include one or more of a bridge, a crown, a coping, and an onlay. The method may include treating a surface of the understructure to improve bonding with the at least one layer. Adding at least one layer may include providing a stationary painting head and digitally controlling a position of the understructure to distribute paint on the functional surface thereof.

In another aspect, a device disclosed herein includes a digital paint head in a substantially fixed location, the digital paint head adapted to selectively deliver at least one material to a paint surface, the at least one material curable into a material suitable for intraoral use; a mounting device, the mounting device adapted to control a position of an understructure for a dental article with at least three translational degrees of freedom and at least two rotational degrees of freedom, the dental article fabricated using an additive process, and the dental article including a volume having a bonding surface shaped to attach to a site in human dentition and a functional surface shaped to replace a dental structure removed from the site; and a controller programmed to receive a shape of the understructure and a description of where to apply the at least one material to a surface of the understructure, and to responsively generate control signals to the digital paint head and the mounting device, thereby digitally painting the understructure.

The digital paint head may be a digital wirejet paint head. The digital paint head may selectively deliver two or more materials by mixing a fluid with two or more different additives. The understructure may include a majority of the volume of the dental article.

In another aspect, a device disclosed herein includes a digital paint head in a substantially fixed rotational orientation, the digital paint head adapted to move with at least one translational degree of freedom and the digital paint head adapted to selectively deliver at least one material to a paint surface, the at least one material curable into a material suitable for intraoral use; a mounting device, the mounting device adapted to control a position of an understructure for a dental article with at least two translational degrees of freedom and at least two rotational degrees of freedom, the dental article fabricated using an additive process, and the dental article including a volume having a bonding surface shaped to attach to a site in human dentition and a functional surface shaped to replace a dental structure removed from the site; and a controller programmed to receive a shape of the understructure and a description of where to apply the at least one material to a surface of the understructure, and to responsively generate control signals to the digital paint head and the mounting device, thereby digitally painting the understructure.

The digital paint head may be a digital wirejet paint head. The at least one translational degree of freedom of the digital paint head may control a distance of the digital paint head from a plane of motion of the mounting device. The understructure may include a majority of the volume of the dental article.

BRIEF DESCRIPTION OF THE FIGURES

The invention and the following detailed description of certain embodiments thereof may be understood by reference to the following figures.

DETAILED DESCRIPTION

Figure 1:
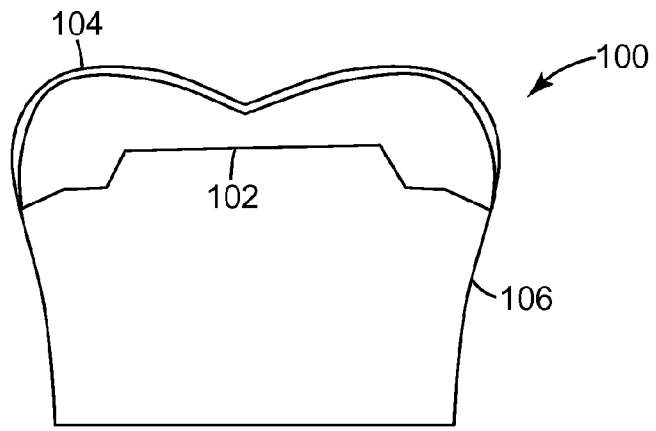
FIG. 1 shows a digitally painted dental article.

Described herein are systems and methods for digitally painting dental objects. While the description emphasizes certain techniques for obtaining three-dimensional models, fabricating understructures for dental articles, and applying surface coatings, it will be understood that additional variations, adaptations, and combinations of the methods and systems below will be apparent to one of ordinary skill in the art, such as fabrication of dental restorations not specifically described, or use of three-dimensional scanning technologies not specifically identified, and all such variations, adaptations, and combinations are intended to fall within the scope of this disclosure. As an example, while the following description emphasizes aesthetic layers upon complete dental articles, the techniques described herein may also, or instead, be applied to an interim article of dental manufacture, such as by applying an adhesive or pre-adhesive coating to a coping before assembly into a crown.

The following description should be read with reference to the drawings, in which like elements in different drawings are numbered in like fashion. The drawings, which are not necessarily to scale, depict selected illustrative embodiments and are not intended to limit the scope of the disclosure. Although examples of construction, dimensions, and materials are illustrated for the various elements, those skilled in the art will recognize that many of the examples provided have suitable alternatives.

Unless explicitly indicated or otherwise clear from the context, the following conventions are employed in the following disclosure, and are intended to describe the full scope of the inventive concepts herein. All numbers expressing feature sizes, amounts, and physical properties used in the specification and claims are to be understood as being modified by the term "about." Any numerical parameters set forth in this specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise. In a list, the term "or" means one or all of the listed elements or a combination of any two or more of the listed elements.

When a group is present more than once in a formula described herein, each group is "independently" selected, whether specifically stated or not. For example, when more than one M group is present in a formula, each M group is independently selected.

The terms "three-dimensional surface representation", "digital surface representation", "three-dimensional surface map", and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

As used herein, the term "room temperature" refers to a temperature of 20° C. to 25° C. or 22° C. to 25° C.

The term "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "dental object", as used herein, is intended to refer broadly to subject matter specific to dentistry. This may include intraoral structures such as dentition, and more typically human dentition, such as individual teeth, quadrants, full arches, pairs of arches which may be separate or in occlusion of various types, soft tissue, and the like, as well as bones and any other supporting or surrounding structures. As used herein, the term "intraoral structures" refers to both natural structures within a mouth as described above and artificial structures such as any of the dental objects described below that might be present in the mouth. As used herein, the term dental article is intended to refer to a man-made dental object. Dental articles may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental articles may also include a "prosthesis" that replaces dentition with removable or permanent structures, such as dentures, partial dentures, implants, retained dentures, and the like. Dental articles may also include "appliances" used to correct, align, or otherwise temporarily or permanently adjust dentition, such as removable orthodontic appliances, surgical stents, bruxism appliances, snore guards, indirect bracket placement appliances, and the like. Dental articles may also include "hardware" affixed to dentition for an extended period, such as implant fixtures, implant abutments, orthodontic brackets, and other orthodontic components. Dental articles may also include "interim components" of dental manufacture such as dental models (full or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects (i.e., dental articles) such as the restorations, prostheses, appliances, hardware, and interim components of dental manufacture as described above. A dental article may be fabricated intraorally, extraorally, or some combination of these.

Terms such as "digital painting", "digital painting process", "computer-controlled painting", "digitally-controlled painting" and the like, as well as verb forms such as "digitally painting", are intended to refer to a computer-controlled painting process, and in particular to such processes that provide for control over a location of paint distribution and a selection among two or more paints for application. A number of technologies may be suitably employed for digital painting provided they can deposit surface layers with sufficient depth, positional accuracy, and material selectively to be usefully employed in coating dental articles. One suitable embodiment may be adapted from Wirejet painting technology formerly available from Pixation Corporation, which applies paint in fluid form. Digitally-controlled wirejet paint heads and systems are described, for example in the following references, each of which is incorporated by reference herein in its entirety: U.S. patent application Ser. No. 08/958,292 to Anderson entitled Metering Device for Paint for Digital Printing filed on Oct. 27, 1997 and issued on Aug. 31, 1999 as U.S. Pat. No. 5,944,893; U.S. patent application Ser. No. 08/878,650 to Anderson entitled Metering Device for Paint for Digital Printing filed on Jun. 19, 1997 and issued on Oct. 26, 1999 as U.S. Pat. No. 5,972,111; U.S. patent application Ser. No. 09/186,220 to Anderson entitled Printer Cartridge filed on Nov. 4, 1998 and issued on Feb. 20, 2001 as U.S. Pat. No. 6,190,454; and U.S. patent application Ser. No. 11/669,387 to Free et al. entitled Printer Having a Print Wire with Alternating Hydrophilic and Hydrophobic Areas to Form Droplets for Printing Inks, filed on Jan. 31, 2007 and published on Aug. 9, 2007 as U.S. Pub. No. 2007/0182797. Any other monochromatic or multichromatic print head suitable for distributing fluids to selected locations of a surface may be similarly employed for digitally-controlled painting. In general, the digital paint head should be capable of delivering paint within a natural dentition color space, either through selective application of different paints or on-the-fly mixing of dyes and other materials. In addition, opacity may be usefully controlled through fillers and other materials within a paint binder. A "digital wirejet paint head" refers specifically to paint heads of the type used in Wirejet printers. More generally, a "digital painting process" may be any of the digital painting techniques described above, or otherwise suitable for use with the systems and methods described herein, including inkjet or laser printing technologies that can be adapted to distribute paints in fluid form. This includes, for example, solid applications, which may be baked to a final coat, or gaseous (e.g., as a gas or as a gaseous suspension) applications such as spray painting. It will be understood that a variety of materials may be applied in fluid form in a digital painting process, including oil-based paints, acrylic paints, urethanes, polyurethanes, enamels, and so forth. A paint as used herein may include pigments for color, binders for structure (e.g., acrylics, polyurethanes, polyesters, melamine resins, epoxy, oil), and solvents or the like for adjusting viscosity (e.g., aliphatics, aromatics, alcohols, ketones, petroleum distillates, esters, glycol ethers, low-molecular weight synthetic resins, etc.), as well as other miscellaneous additives to control handling properties or provide improved performance in applied paint (e.g., antifreeze, antibacterials, pigment stability, etc.). Paints may also be categorized according to curing mechanism, which may, for example, include drying by solvent evaporation, oxidative crosslinking, catalyzed polymerization, and coalescence. In the typical dental applications described herein, any such material that can be applied in fluid form may be used, provided it can be dried, heated, or otherwise cured into a surface suitable for use in a dental article.

FIG. 1 shows a dental article that can be fabricated using the techniques described herein. While the dental article 100 depicted in FIG. 1 is a crown, it will be understood that any of the dental articles described above may be similarly prepared using the techniques described herein.

The dental article 100 includes an understructure 102 and an outer layer 104 formed using any of the digital painting techniques described herein. In general, the understructure 102 may include a majority of the volume of the dental article 100 and provide structural support and strength thereto. The outer layer 104 may be formed of any material suitable for intraoral use, and may provide a surface finish consistent with the aesthetics and function of the tooth structure being replaced. After fabrication is complete, the dental article 100 is seated on a mating, prepared tooth surface of a tooth 106. FIG. 1 should not be understood as limiting. The tooth 106 may be any tooth including a molar, pre-molar, canine, and incisor. Similarly, the dental article 100 may be a restoration (such as a crown, an inlay, an onlay, or a veneer), a prosthesis (such as a denture, or an implant), or any other dental article that might usefully receive an outer layer 104 using the techniques described herein.

Figure 2:
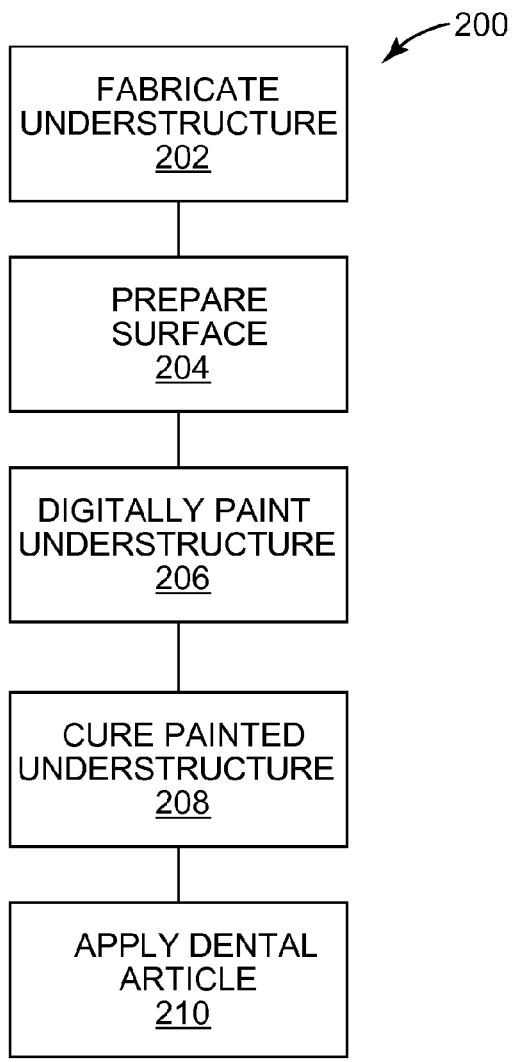
FIG. 2 shows a process for digitally painting a dental article.

FIG. 2 shows a process 200 for digitally painting a dental article. The process may begin by fabricating an understructure as shown in step 202. There are a wide variety of materials and techniques for fabricating dental articles that may be suitably employed with the systems and methods described herein.

The fabrication may be performed using rapid fabrication techniques such as stereolithography, digital light processing, three-dimensional printing, and computerized milling. In general, these techniques rely on a digital, three-dimensional model of dentition to drive operation of the rapid fabrication equipment. In some instances, the model may be obtained by direct scanning of dentition, including three-dimensional models of dentition before and after preparation of a tooth surface for the dental article. In other instances, a digital model may be obtained from an extra-oral scan of a physical impression of dentition using, e.g., conventional impressioning techniques to capture a reverse mold of the region or regions of interest. Scanning may be performed with any suitably accurate three-dimensional scanning system. Suitable video-based scanning systems are described for example in the following patent applications, each of which is incorporated by reference herein in its entirety: U.S. patent application Ser. No. 11/270,135 to Zhang et el. entitled Determining Camera Motion, filed on Nov. 9, 2005 and published on May 10, 2007 as U.S. Pub. No. 2007/0103460; U.S. patent application Ser. No. 11/469,869 to Kriveshko et al. entitled Superposition for Visualization of Three-Dimensional Data Acquisition, filed on Sep. 3, 2006 and published on Jul. 26, 2007 as U.S. Pub. No. 2007/0172101; and U.S. patent application Ser. No. 11/530,420 to Rohály et al. entitled Three-Channel Camera Systems with Collinear Apertures, filed on Sep. 8, 2006 and published on Aug. 16, 2007 as U.S. Pub. No. 2007/0188769. Other three-dimensional scanning techniques are known for three-dimensional image acquisition including technologies based upon structured light, laser scanning, direct ranging, and so forth. Any such technology that can be adapted to obtain three-dimensional models of suitable accuracy and precision for fabricating dental articles may be used with the systems and methods described herein. However obtained, it will be understood that a digital model for an understructure may be compensated for physical constraints such as material shrinkage, cementation voids, and thickness of layers of paint or other finish materials applied to the understructure.

Direct capture of three-dimensional surface data may be useful for providing many types of data useful in fabricating an article, such as data concerning how to mate an article to a prepared tooth surface, how to shape an article to match removed tooth surfaces, and how to adapt an article for use with surrounding teeth. However, it should also be appreciated that numerous other techniques are known for fabrication of dental articles. For example, dental articles such as crowns, inlays, onlays, and the like have traditionally been fabricated using physical impressions of human dentition taken with various elastomers and other materials. These impressions are subsequently cut into working dies for direct, manual fabrication of dental articles therefore. There are also numerous techniques for direct fabrication of a dental article using self-supporting, malleable, curable materials such as those described in the following U.S. patent applications, each of which is incorporated by reference in its entirety: U.S. patent application Ser. No. 10/921,648 to Karim et al. entitled Hardenable Dental Article and Method of Manufacturing the Same, filed on Aug. 19, 2004 and published on May 12, 2005 as U.S. Pub. No. 2005/0100868; U.S. patent application Ser. No. 10/749,306 to Karim et al. entitled Curable Dental Mill Blanks and Related Methods, filed on Dec. 31, 2003 and published on Jul. 7, 2005 as U.S. Pub. No. 2005/0147944; U.S. patent application Ser. No. 10/643,771 to Kvitrud et al. entitled Dental Crown Forms and Methods, filed on Aug. 19, 2003 and published on Feb. 24, 2005 as U.S. Pub. No. 2005/0042577; U.S. patent application Ser. No. 10/643,748 to Oxman et al. entitled Dental Article Forms and Methods, filed on Aug. 19, 2003 and published on Feb. 24, 2005 as U.S. Pub. No. 2005/0042576; U.S. patent application Ser. No. 10/219,398 to Karim et al. entitled Hardenable Self-Supporting Structures and Methods, filed on Aug. 15, 2002 and published on Jun. 19, 2003 as U.S. Pub. No. 2003/0114553; and International Patent Application No. US06/016197 to Karim et al. entitled Malleable Symmetric Dental Crowns.

Any of these techniques, or combinations thereof, as well as other techniques, may be employed to fabricate an understructure in step 202. In general, the term "additive" when used in reference to fabrication is intended to refer to processes other than milling, which is referred to herein as a "subtractive" process. Other "subtractive" processes may be employed to remove material from a workpiece such as abrading, polishing, controlled vaporization, electronic discharge milling (EDM), cutting by water jet or laser or any other method of cutting, removing, shaping or carving material. In general, the use of SMC materials that are manually shaped or otherwise assembled into a desired form are considered "additive" for the purposes of this disclosure unless a milling process or other digitally-controlled subtractive process is employed in the shaping of such materials into a dental article. However fabricated, the process 200 may proceed to step 204 where a surface of the understructure is prepared for painting.

A variety of preparation steps may be employed in step 204. The understructure may be dried, particularly where fabrication employed fluids, such as with milling lubricants. The understructure may be trimmed from any supporting structures, and sanded or otherwise smoothed. Where curable materials are employed, the understructure may be partially or fully cured. In addition, a sealant or primer may be applied to the understructure prior to the application of aesthetic or functional paint layers.

After preparing the surface, the process 200 may proceed to step 206 where the understructure is digitally painted. A number of suitable digital painting technologies are described above.

In general, a variety of fluids may be usefully employed to digitally paint a dental article. This may include porcelain, resins, acrylic polymers, and any other suitable material. Using a digitally controlled painting process, an outer layer for the understructure may be applied with different colors in different areas. In addition, multiple layers may be applied with varying colors and opacities to build a surface closely resembling natural dentition. In one aspect, visual information concerning color may be captured from a dental patient's natural dentition, and this color information may be applied to create a corresponding surface on the dental article. Various dyes may be used to obtain different colors, which dyes may be provided to a digital painter as a number of discrete paint source selections, or may be added as paint is distributed from a paint head to permit computer-controlled color generation. In other embodiments, paints having different discrete colors may be applied by two or more paint heads or print heads concurrently to obtain a mixed color. The digital painting system may provide a movable paint head, or the dental article may be secured to a movable mount that provides translation and rotation along a number of axes so that areas on the surface of the dental article can be selectively positioned in front of a fixed paint head. In either case, a digital model of the understructure may be employed to control positioning. The digital painting system may also, or instead, include position or range detection to help ensure accurate distribution of paint on a target article.

After digitally painting an outer layer onto the understructure, the process 200 may proceed to step 208 where the painted understructure is cured.

It will be understood that curing may depend in large part on the materials used for the understructure and outer layer. The understructure may require curing by heat, light, pressure, or the like to achieve desired structural strength. In addition, the outer layer may cure through evaporation of solvents, thinners and the like, or may require heat, light, pressure, vacuum, electromagnetic waves or the like to initiate or quicken polymerization or other curing processes depending, of course, on the nature of the materials used in the outer layer. Curing may be achieved or accelerated by two or more cycles of curing conditions.

The painted and cured dental article may finally be applied to a tooth stump or the like for final use, as shown in step 210. This may include any conventional finishing steps including test fitting, adjustment, cementation, and the like.

It will be understood that the preceding description is a non-limiting example, and that numerous variations in materials and steps may be employed in a digital painting process as described herein. For example, after a digital paint layer is fully cured, one or more additional layers (each possibly having different colors and opacities in different regions) may be applied, with subsequent curing to the additional layer(s). In another embodiment, a layer may be partially cured before addition of another layer. All such variations as would be apparent to one of ordinary skill in the art are intended to fall within the scope of this disclosure.

Figure 3:
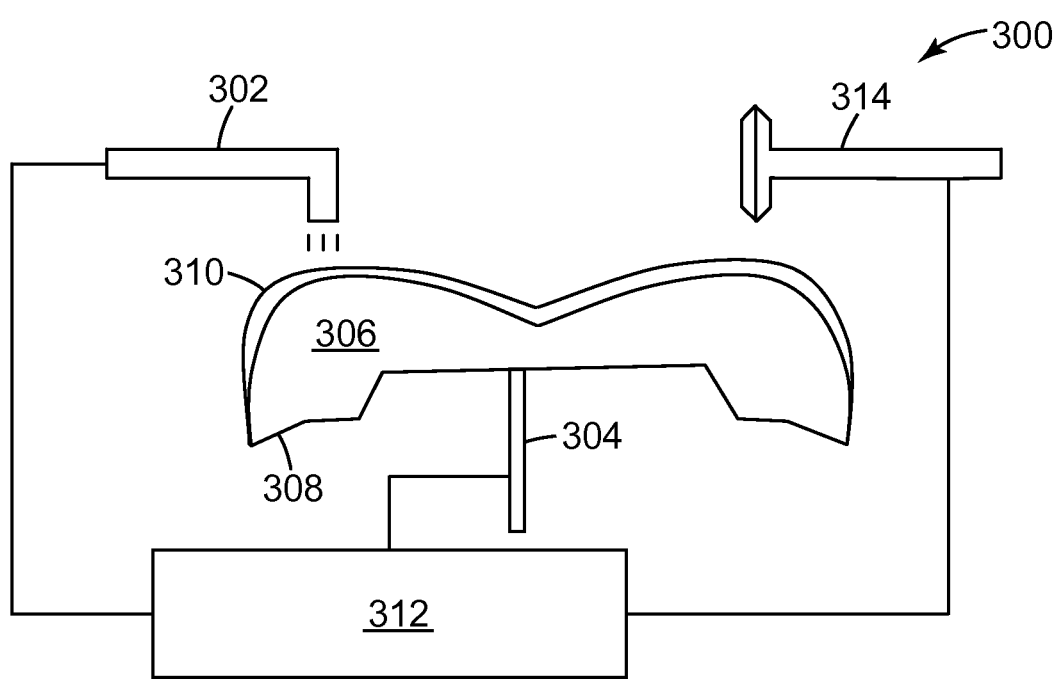
FIG. 3 shows a device for digitally painting a dental article.

FIG. 3 shows a device 300 for digitally painting a dental article. In general, the device 300 includes a digital paint head 302, a mounting device 304 holding a dental article 306 that has a bonding surface 308 and a functional surface 310, and a controller 312. The device 300 may also incorporate a milling machine 314 or other cutting tool.

The digital paint head 302 may be any device coupled to a digital painting system for digitally-controlled distribution of paint. The digital painting system may provide for computer control of type of paint, dye mixture, thinning, and so forth, and may also or instead provide computer selection among two or more different paints for application at a particular location. In one aspect, the digital paint head 302 may itself have a controllable position so that the head 302 can be steered over a three-dimensional surface to be painted, or the digital paint head 302 may remain fixed while an object is moved (under computer control) beneath it. The digital paint head 302 may apply paint as droplets, a gaseous suspension, a fluid stream, or in any other manner suitable for controlling distribution on a target. Also as noted above, any substance suitable for use as a coating of dental articles and available in a fluid form may be employed with the digital paint head 302 described herein. In one aspect, the digital paint head may be a digitally-controlled wirejet paint head as described above. Any other monochromatic or multichromatic print head suitable for distributing fluids to selected locations of a surface may be similarly employed. In general, the digital paint head should be capable of delivering paint within a natural dentition color space, either through selective application of different paints or on-the-fly mixing of dyes and other materials. In addition, opacity may be usefully controlled through fillers and other materials within a paint binder.

The mounting device 304 may be any device suitable for retaining the dental article 306 in a desired position. This may include clamps, grips, adhesives, mechanical friction fits (which may be machined into the dental article 306), and so forth. In one aspect, the mounting device 304 may retain the dental article 306 in a substantially fixed position. In another aspect, the mounting device 304 may be operable to move the dental article 306 in translation or rotation among any number of axes in order to position a desired point on a surface of the dental article 306 beneath the paint head 302 (or the cutting tool 314). Three translational degrees of freedom and two rotational degrees of freedom may be provided with suitable electromechanical components, and may suffice for any surface of the dental article 306 to be coated with a stationary paint head. In another aspect, motion control may be distributed across the digital paint head 302 and mounting device 304. Thus for example the mounting device 304 may impart a controlled rotational orientation to the dental article 312 around a single axis, while the digital paint head 302 can be translated along two axes (e.g., parallel to the rotational axis, and orthogonal to the rotational axis) so that combined motion of the mounting device 304 and digital paint head 302 can position the paint head 302 to apply paint to any surface region of the dental article 306. In another embodiment, the digital paint head 302 may have a single translational degree of freedom that controls, for example, a distance of the digital paint head 302 from a plane of motion provided by two translational degrees of freedom of the mounting device 304.

The dental article 306, which may be any of the dental articles described above, may include a bonding surface 308 and a functional surface 310. The bonding surface 308 may be shaped to fit onto a mating prepared tooth surface in a dental patient's dentition. The form of the bonding surface 308 may be determined for example through physical impressioning or scanning of the prepared tooth surface. The functional surface 310 may replace a surface of a natural tooth with corresponding structural and aesthetic properties. The functional surface 310 may be formed of any substance suitable for, or curable into a form suitable for, intraoral use, and may be constructed using the digital painting techniques described herein.

The controller 312 may communicated with the digital paint head 302 (or an associated digital painting system) to control distribution of paint to the dental article 306. This may include selective application of different paints to different locations of the dental article, as well as selective application of different paints to different layers of the functional surface 310, which may be formed from any number of digitally painted layers. The controller 312 may control a position of the digital paint head 302, or may control a position of the mounting device 304 so that different surfaces of the dental article 306 are exposed to the paint head. In positioning the dental article 306, the controller 312 may employ a digital, three-dimensional model of the dental article 306, along with information concerning the color, opacity, texture, and the like of the dental article 306 along the surface thereof. It will be understood that while the digital paint head 302 is intended for coating the functional surface 310 of the dental article 306, the paint head may also, or instead, be usefully employed to apply sealants, adhesives, adhesive precursors, or any other useful materials to the bonding surface 308 or the functional surface 310.

It will be appreciated that the controller and processes performed by the controller may be realized in hardware, software, or any combination of these suitable for the data acquisition and fabrication technologies described herein. This includes realization in one or more microprocessors, microcontrollers, embedded microcontrollers, programmable digital signal processors or other programmable devices, along with internal and/or external memory. The realization may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as the controller 312 and digital paint head 302 (and cutting tool 314) in a number of ways or all of the functionality may be integrated into a dedicated, standalone device. All such permutations and combinations are intended to fall within the scope of the present disclosure.

A cutting tool 314 may usefully be included in the device 300, and have an associated digitally-controlled milling machine or similar hardware. The cutting tool 314 may operate under control of the controller to shape one or more surface of the dental article 306, either by moving the cutting tool 314 or by moving the dental article 306 with a movable mount 304, or some combination of these. While a single cutting tool 314 is illustrated, it will be appreciated that many computerized milling machines provide a number of cutting tools and/or a cutting tool with interchangeable cutting instruments having different roughness, hardness, and shape. As with the digital paint head 302, the cutting tool 314, or an associated milling machine, or the controller 312, may use a three-dimensional model of the dental article to control material removal from surfaces of the dental article 306. In an embodiment, the device 300 may be employed to receive a mill blank, shape the mill blank, and finish the shaped article with one or more layers of paint, all under control of the controller 312.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. A method comprising:
    fabricating an understructure for a dental article using an additive process by forming the understructure from a self-supporting, malleable, curable material;
    preparing the understructure for painting by partially curing the understructure;
    milling the understructure to form the understructure for the dental article according to a digital model for the understructure that compensates for a thickness of layers of finish material to be applied to the understructure, the dental article including a volume having a bonding surface shaped to attach to a site in human dentition and a functional surface shaped to replace a dental structure removed from the site;
    painting a plurality of layers on to the functional surface of the understructure to provide an aesthetic finish using a digitally-controlled paint head and a mounting device collectively operable to move the dental article with three translational degrees of freedom and two rotational degrees of freedom relative to the digitally-controlled paint head;
    controlling a selection from among at least two paints for application by the digitally-controlled paint head to the understructure, the plurality of layers including layers with varying colors and opacities selected to build a surface closely resembling natural dentition based upon information concerning color captured from a dental patient's natural dentition; and
    fully curing the understructure.

2. The method of claim 1 wherein the understructure includes a majority of the volume of the dental article.

3. The method of claim 1 further comprising receiving a digital model of the dental article and digitally fabricating the understructure from the digital model.

4. The method of claim 1 wherein the plurality of layers includes two or more different materials.

5. The method of claim 4 wherein the two or more different materials have a color and an opacity selected to provide the dental article with an appearance similar to the dental structure removed from the site.

6. The method of claim 1 wherein adding at least one layer includes adding at least one layer to the functional surface that includes two or more different materials in two or more regions of the functional surface.

7. The method of claim 6 wherein the two or more different materials each have a different opacity.

8. The method of claim 6 wherein the two or more different materials each have a different color.

* * * * *